US006964238B2

(12) United States Patent
Mortell et al.

(10) Patent No.: US 6,964,238 B2
(45) Date of Patent: Nov. 15, 2005

(54) PROCESS FOR MAKING A GARMENT HAVING HANGING LEGS

(75) Inventors: Heather S. Mortell, Neenah, WI (US); Joseph D. Coenen, Kaukauna, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 2 days.

(21) Appl. No.: 10/750,592

(22) Filed: Dec. 31, 2003

(65) Prior Publication Data

US 2005/0145150 A1 Jul. 7, 2005

(51) Int. Cl.[7] .................. D05B 25/00; D05B 37/00; A61F 13/74
(52) U.S. Cl. ................... 112/475.09; 604/393
(58) Field of Search ............... 112/475.09, 475.08, 112/475.06, 413, 303, 304, 307, 470.33, 129, 112/147, 153; 2/113, 114, 400, 401, 236; 156/164, 93; 493/194; 428/137; 604/393–402, 604/385.01, 385.11, 385.125, 391; 83/13, 83/14, 55, 935, 913, 936

(56) References Cited

U.S. PATENT DOCUMENTS

| | | | |
|---|---|---|---|
| 3,678,516 A | | 7/1972 | Backer |
| 3,873,999 A | * | 4/1975 | Artzt ........................ 2/113 |
| 4,663,106 A | | 5/1987 | Pomplun et al. |
| 4,663,220 A | | 5/1987 | Wisneski et al. |
| 4,665,306 A | | 5/1987 | Roland et al. |
| 4,704,116 A | | 11/1987 | Enloe |
| 4,786,346 A | | 11/1988 | Ales et al. |
| 4,801,345 A | * | 1/1989 | Dussaud et al. ........... 156/164 |
| 4,816,094 A | | 3/1989 | Pomplun et al. |
| 4,896,618 A | * | 1/1990 | Blake et al. ........... 112/475.06 |
| 4,946,539 A | | 8/1990 | Ales et al. |
| 5,046,272 A | | 9/1991 | Vogt et al. |
| 5,226,992 A | | 7/1993 | Morman |
| 5,500,063 A | | 3/1996 | Jessup |
| 5,545,158 A | | 8/1996 | Jessup |
| 5,669,996 A | | 9/1997 | Jessup |
| 6,010,586 A | | 1/2000 | Suprise |
| 6,098,557 A | | 8/2000 | Couillard et al. |
| 6,149,637 A | | 11/2000 | Allen et al. |
| 6,192,521 B1 | | 2/2001 | Alberts et al. |
| 6,432,243 B1 | * | 8/2002 | Popp et al. ............... 156/204 |
| 6,458,116 B1 | | 10/2002 | Matsushita |
| 6,482,278 B1 | * | 11/2002 | McCabe et al. ........... 156/73.1 |
| 6,550,288 B2 | | 4/2003 | Browder, Jr. et al. |
| 6,585,840 B2 | | 7/2003 | Rabe et al. |
| 6,651,463 B2 | | 11/2003 | Bonnin |

(Continued)

FOREIGN PATENT DOCUMENTS

EP         0 217 032 B1      2/1992

(Continued)

OTHER PUBLICATIONS

US 5,915,536, 06/1999, Alberts et al. (withdrawn)

Primary Examiner—Ismael Izaguirre
(74) Attorney, Agent, or Firm—John L. Brodersen

(57) ABSTRACT

A distinctive process for making a garment having a waist opening and a pair of hanging legs is disclosed. The process includes providing a first web and a second web and joining the first web and the second web to provide a crotch seam. Portions of the webs may also be removed to provide a crotch gap. The first web is drawn from the second web and at least a portion of the webs are slit to provide a garment chassis. Edges of the garment chassis may be fastened together to provide the garment.

34 Claims, 5 Drawing Sheets

U.S. PATENT DOCUMENTS

| | | |
|---|---|---|
| 6,685,613 B1 * | 2/2004 | Stopher et al. ............ 493/194 |
| 2003/0088955 A1 | 5/2003 | Bridges |
| 2003/0115660 A1 | 6/2003 | Hopkins |
| 2003/0217407 A1 | 11/2003 | Andrews-Jones |
| 2004/0098791 A1 | 5/2004 | Faulks |
| 2004/0102746 A1 | 5/2004 | Mortell et al. |
| 2004/0107481 A1 | 6/2004 | Mortell et al. |

FOREIGN PATENT DOCUMENTS

| | | |
|---|---|---|
| EP | 1 048 231 A1 | 11/2000 |
| EP | 1 060 677 A1 | 12/2000 |
| EP | 1 108 371 A1 | 6/2001 |
| EP | 1 108 372 A1 | 6/2001 |
| EP | 1 188 427 A1 | 3/2002 |
| JP | 2001-172802 A | 6/2001 |
| JP | 2001-254202 A | 9/2001 |
| WO | WO 01/87217 A2 | 11/2001 |
| WO | WO 01/87218 A2 | 11/2001 |
| WO | WO 01/87562 A2 | 11/2001 |
| WO | WO 01/87753 A2 | 11/2001 |
| WO | WO 01/88245 A2 | 11/2001 |
| WO | WO 02/49565 A2 | 6/2002 |
| WO | WO 2002/067833 A1 | 9/2002 |
| WO | WO 2003/041625 A1 | 5/2003 |
| WO | WO 2004/073430 A2 | 9/2004 |

* cited by examiner

PROCESS FOR MAKING A GARMENT HAVING HANGING LEGS

FIELD OF THE INVENTION

The present invention relates generally to a process for making garments to be worn about the lower torso, and particularly to a process for making a garment having hanging legs. Still more particularly, the present invention relates to a process for making boxer shorts.

BACKGROUND OF THE INVENTION

Garments having hanging legs such as boxer shorts or other pant-like garments have a variety of uses including semi-durable garments, disposable garments, and swimwear. In particular configurations, the garment may include an absorbent body; in such configurations, the garments may have applications as training pants, incontinence products, feminine care products, and the like.

Processes for making such garments are known in the art. Nonetheless, the processes that are presently available often result in garments that are not aesthetically pleasing, or do not provide a comfortable fit, or both. In particular, such processes often do not produce garments having a traditional crotch (i.e. a front to back crotch with significant crotch depth), or with hanging legs. Moreover, such processes can often be complex, or may not lend themselves to continuous high-speed converting, or further may not be suitable for including an absorbent in the garment.

Accordingly, there remains a need for a process that provides garments having hanging legs and traditional boxer styling and shape. Further, there is a need for a process that provides such garments with a front to back crotch seam that provides suitable crotch depth. Still further, there is a need for a process for making such garments that is capable of being used in connection with an automated high-speed converting system. Moreover, there is a need for such a process that may optionally produce garments with an absorbent.

SUMMARY OF THE INVENTION

In one aspect, the present invention is directed to a process for making a garment having a waist opening and a pair of hanging legs. The process defines a machine direction, a cross-machine direction and an orthogonal direction that is perpendicular to a plane created by the machine direction and the cross-machine direction. The process includes providing a first web defining a first web waist edge, a first web leg edge, a first leading chassis edge, a first web interior surface and a first web exterior surface. The process also includes providing a second web defining a second web waist edge, a second web leg edge, a second leading chassis edge, a second web interior surface and a second web exterior surface, the second web interior surface being disposed in a facing relationship with the first web interior surface. The process also includes joining the first web to the second web to provide a crotch seam and selectively removing a portion of the first web at the first web waist edge and a portion of the second web at the second web waist edge to form a crotch gap. The process further includes drawing the first web from the second web in the cross-machine direction, slitting at least a portion of the first web between the first web leg edge and the first web waist edge, and slitting at least a portion of the second web between the second web leg edge and the second web waist edge. The slitting of the first web and the second web can provide a first trailing chassis edge, a second trailing chassis edge and defines a garment chassis includes the first web and the second web between the first and the second leading and trailing chassis edges and joined at the crotch seam. The process can further include fastening the first leading chassis edge to the first trailing chassis edge and the second leading chassis edge to the second trailing chassis edge to provide the garment having the waist opening and the pair of hanging legs.

In another aspect, the present invention is directed to a continuous process for making garments having a waist opening and a pair of hanging legs, the process defining a machine direction, a cross-machine direction and an orthogonal direction that is perpendicular to a plane created by the machine direction and the cross-machine direction. The process includes providing a first web traveling in a machine direction and defining a first web waist edge, a first web leg edge, a first leading chassis edge, a first web interior surface and a first web exterior surface. The process also includes providing a second web traveling in a machine direction and defining a second web waist edge, a second web leg edge, a second leading chassis edge, a second web interior surface and a second web exterior surface, the second web interior surface being disposed in a facing relationship with the first web interior surface. The process also includes joining the first web to the second web at a crotch seam, selectively removing a portion of the first web at the first web waist edge and a portion of the second web at the second web waist edge to provide a crotch gap, and drawing the first web from the second web in the cross-machine direction to define a leading garment waist edge and a trailing garment waist edge. The process further includes slitting at least a portion of the first web between the first web leg edge and the first web waist edge, and a portion of the second web between the second web leg edge and the second web waist edge. The slitting of the first web and the second web provides a first trailing chassis edge, a second trailing chassis edge and defines a garment chassis includes the first web and the second web between the first and the second leading and trailing chassis edges and joined at the crotch seam. The process also includes fastening the first leading chassis edge to the first trailing chassis edge and the second leading chassis edge to the second trailing chassis edge to provide the garment having the waist opening and the pair of hanging legs.

In another aspect, the present invention is directed to a continuous process for making garments having a waist opening and a pair of hanging legs, the process defining a machine direction, a cross-machine direction and an orthogonal direction that is perpendicular to a plane created by the machine direction and the cross-machine direction. The process includes providing a first web traveling in a machine direction and defining a first web waist edge, a first web leg edge, a first leading chassis edge, a first web interior surface and a first web exterior surface. The process also includes providing a second web traveling in a machine direction and defining a second web waist edge, a second web leg edge, a second leading chassis edge, a second web interior surface and a second web exterior surface, the second web interior surface being disposed in a facing relationship with the first web interior surface. The process also includes joining the first web to the second web at selected locations to provide a plurality of spaced crotch seams, removing portions of the first web at the first web waist edge and corresponding portions of the second web at the second web waist edge to provide a plurality of crotch gaps, and drawing the first web from the second web in the cross-machine direction to define a leading garment waist edge and a trailing garment waist edge. The process further includes slitting at least a portion of the first web between the first web leg edge and the first web waist edge, and a portion of the second web between the second web leg edge and the second web waist edge. The slitting of the first web and the second web provides a first trailing chassis edge, a second trailing chassis edge and defines a garment chassis includes the first web and the second web between the first and the second leading and trailing chassis edges and joined at a crotch seam. The process further includes extending the garment chassis in the machine direction to elongate the garment chassis and attaching an absorbent assembly to the garment chassis, where the absorbent assembly is disposed along the crotch seam. Still further, the process includes separating the garment chassis from the first web and the second web, and fastening the first leading chassis edge to the first trailing chassis edge and the second leading chassis edge to the second trailing chassis edge to provide the garment having the waist opening and the pair of hanging legs.

In yet another aspect, the present invention is directed to a process for making garments, the process defining a machine direction, a cross-machine direction and an orthogonal direction that is perpendicular to a plane created by the machine direction and the cross-machine direction. The process includes providing a first web defining a first web waist edge, a first web leg edge, a first leading chassis edge, a first web interior surface and a first web exterior surface. The process also includes providing a second web defining a second web waist edge, a second web leg edge, a second leading chassis edge, a second web interior surface and a second web exterior surface, the second web interior surface being disposed in a facing relationship with the first web interior surface. The process also includes joining the first web to the second web to provide a crotch seam, selectively removing a portion of the first web at the first web waist edge and a portion of the second web at the second web waist edge to form a crotch gap, and drawing the first web from the second web in the cross-machine direction. The process further includes slitting at least a portion of the first web between the first web leg edge and the first web waist edge, and slitting at least a portion of the second web between the second web leg edge and the second web waist edge. The slitting of the first web and the second web provides a first trailing chassis edge, a second trailing chassis edge and defines a garment chassis includes the first web and the second web between the first and the second leading and trailing chassis edges and joined at the crotch seam.

In still yet another aspect, the present invention is directed to a process for making garments having a waist opening and a pair of hanging legs. The process includes providing a first web traveling in a machine direction, providing a second web traveling in a machine direction, and joining spaced portions of the first and second webs to define a plurality of crotch seams. The process also includes selectively removing portions of the first and second webs to provide a plurality of crotch gaps, drawing the first web from the second web in a cross-machine direction at locations disposed between successive crotch gaps, and slitting the first web and the second web between successive crotch gaps to form a plurality of garment chasses, each garment chassis includes a first web portion and a second web portion joined at a crotch seam. Still further, the process includes fastening the first web portion to itself and the second web portion to itself to form a garment having a waist opening and a pair of hanging legs.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

DEFINITIONS

Figure 1:
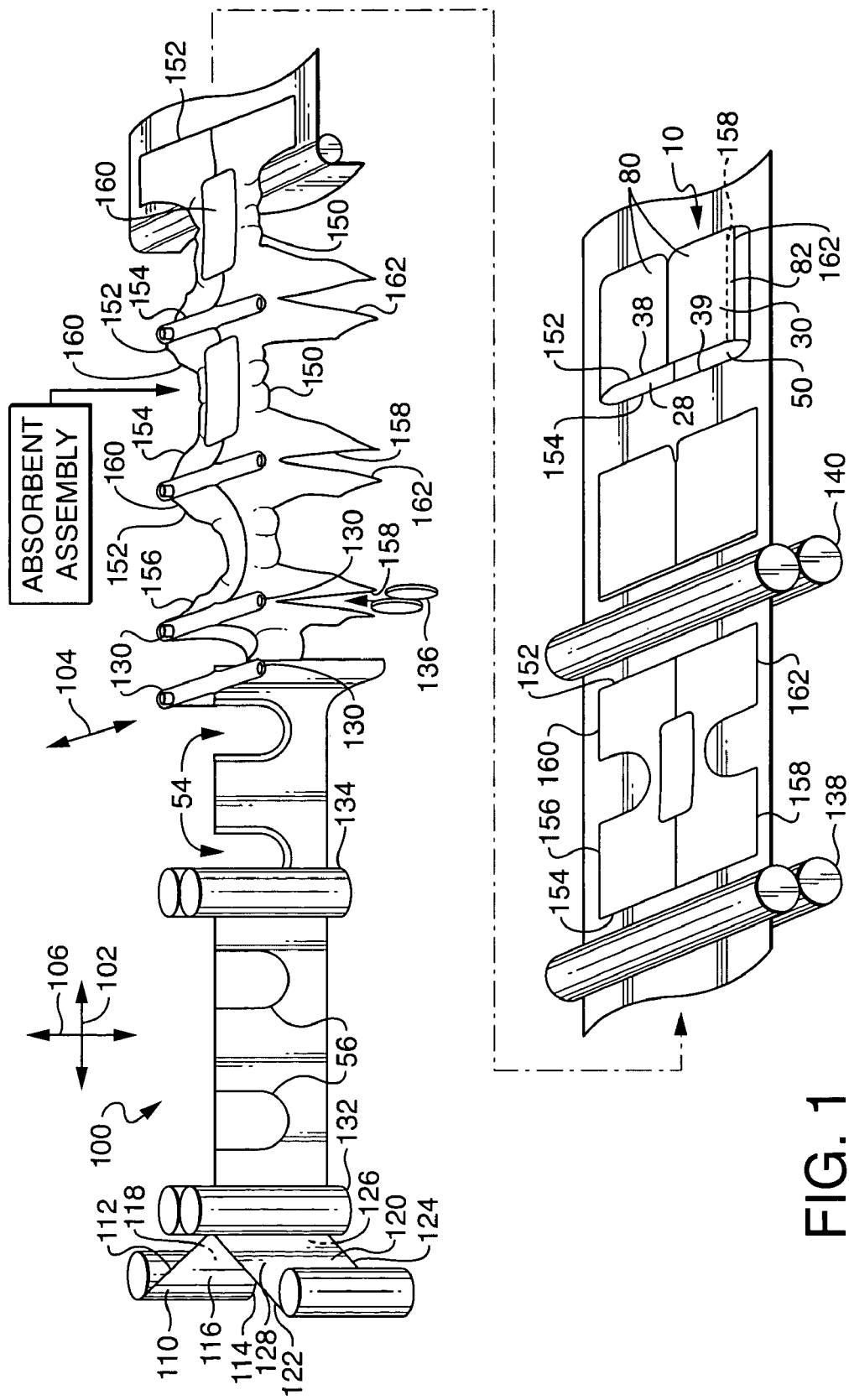
FIG. 1 representatively illustrates a schematic view of one aspect of a process of the present invention.

Within the context of this specification, each term or phrase below will include the following meaning or meanings.

"Attached" refers to the joining, adhering, connecting, bonding, sewing together, or the like, of two elements. Two elements will be considered to be attached together when they are attached directly to one another or indirectly to one another, such as when each is directly attached to intermediate elements. The term "attached" includes permanent and refastenable attachment. In addition, the attachment can be completed either during the manufacturing process or by the end user.

"Bonded" refers to the joining, adhering, connecting, attaching, sewing together, or the like, of two elements. Two elements will be considered to be bonded together when they are bonded directly to one another or indirectly to one another, such as when each is directly bonded to intermediate elements.

"Boxer shorts" or "Shorts" refers to a pant, trunks, briefs, and the like, that are relatively loose fitting at the leg area.

"Comprising" is inclusive or open-ended and does not exclude additional, unrecited elements or method steps.

"Connected" refers to the joining, adhering, bonding, attaching, sewing together, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent of its relaxed length and will recover, upon release of the applied force, at least 10 percent of its elongation. It is generally preferred that an elastic material or composite be capable of being elongated by at least 100 percent, more preferably by at least 300 percent, of its relaxed length and recover, upon release of an applied force, at least 50 percent of its elongation.

"Fabrics" is used to refer to all woven, knitted and nonwoven fibrous webs.

"Front-to-back crotch seam" refers to a seam extending from the front region to the back region of a pant-style garment, through the crotch region. The seam can join two separate pieces of material, or separate edges of a single piece of material.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the direction in which material travels during a production process, as opposed to "cross-machine direction" which refers to the direction generally perpendicular to the machine direction.

"Member" when used in the singular can have the dual meaning of a single element or a plurality of elements.

"Nonwoven" and "nonwoven web" refer to materials and webs of material that are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Pants" includes full length and short pants.

"Stretchable" means that a material can be stretched, without breaking, by at least 25% (to 125% of its initial (unstretched) length) in at least one direction, suitably by at least 100% (to 200% of its initial length), desirably by at least 150% (to at least 250% of its initial length).

These terms may be defined with additional language in the remaining portions of the specification.

DETAILED DESCRIPTION

Figure 2:
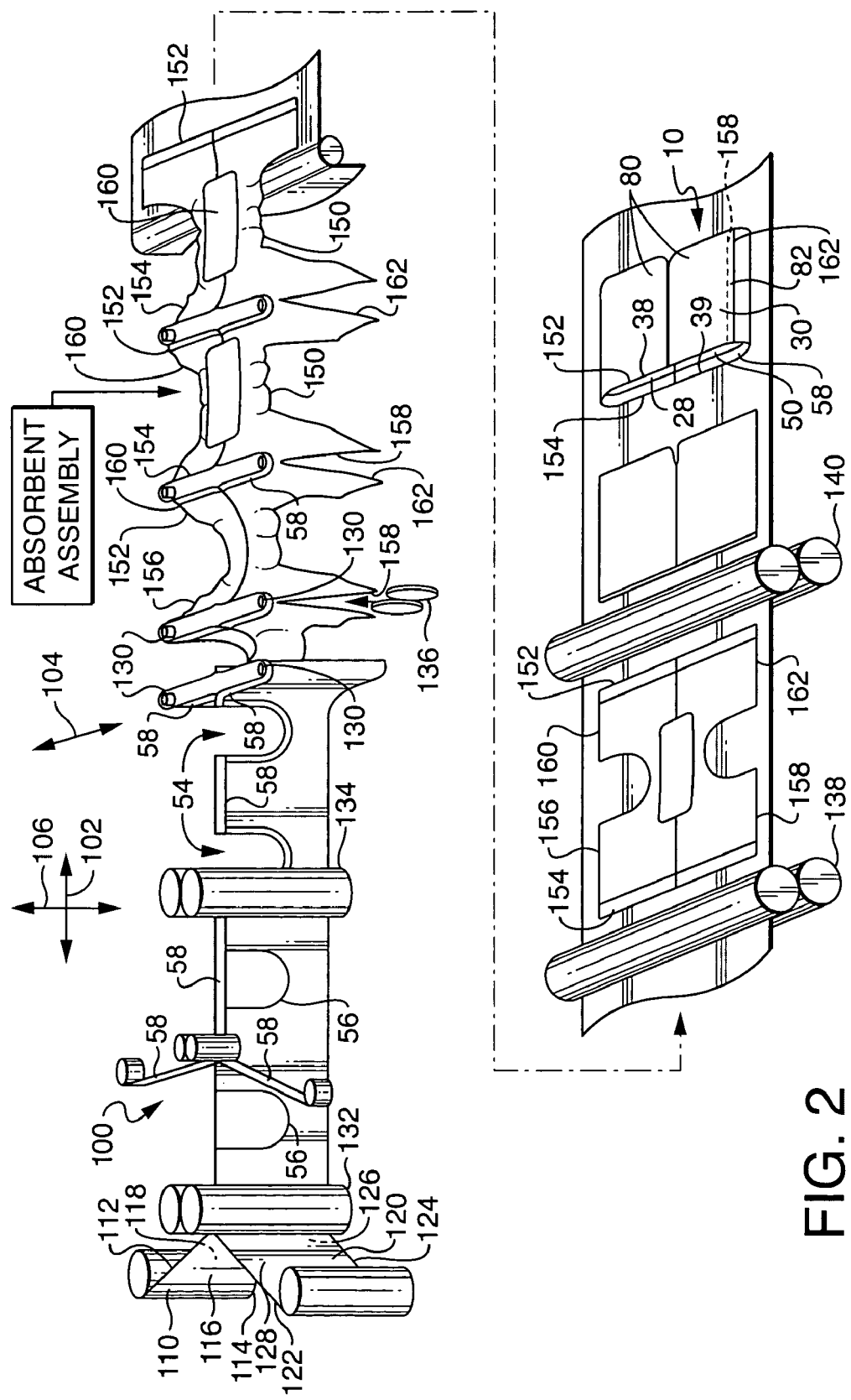
FIG. 2 representatively illustrates a schematic view of another aspect of the process of the present invention similar to FIG. 1 including applying waist elastics.
Figure 3:
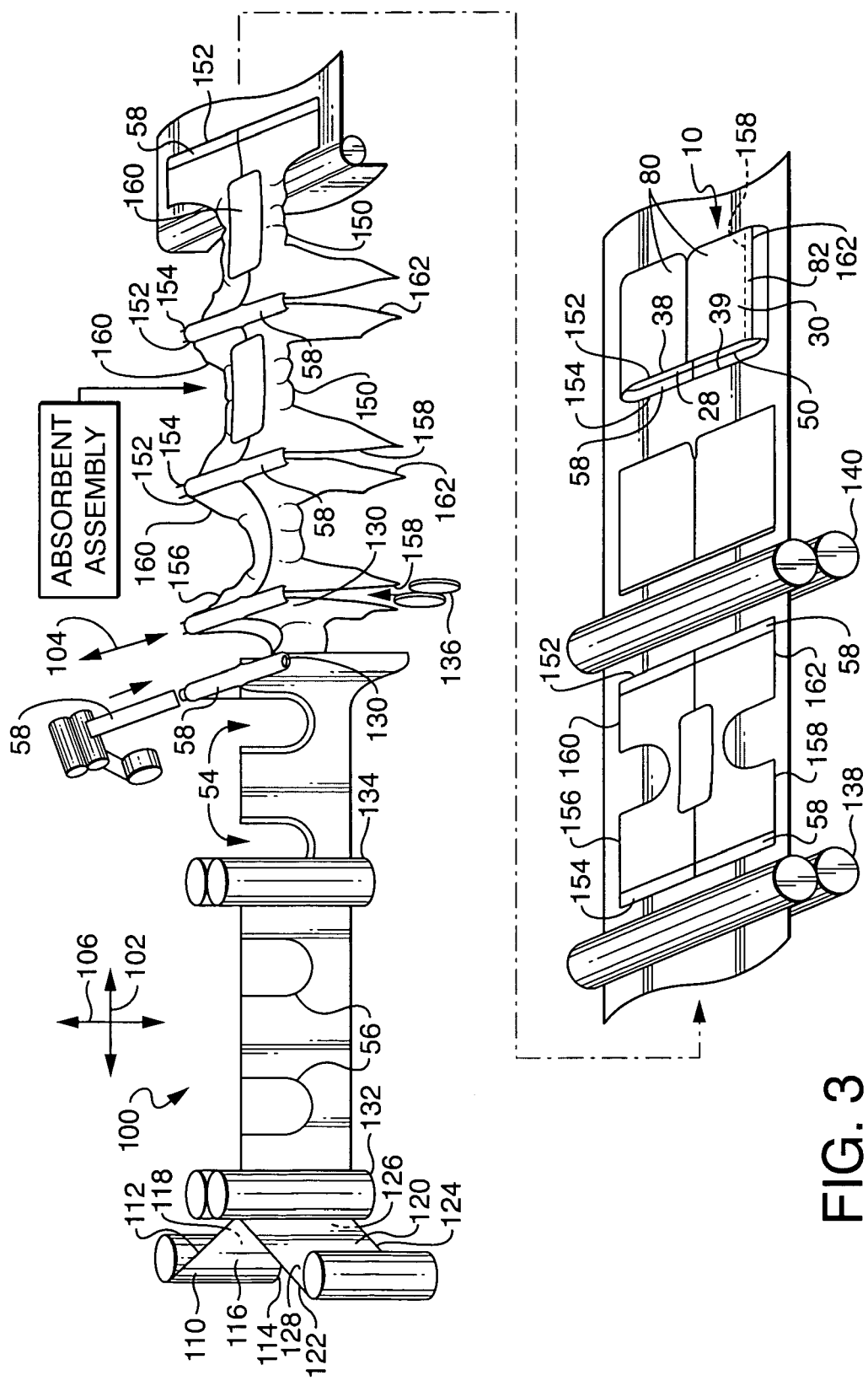
FIG. 3 representatively illustrates a schematic view of a process similar to FIG. 2 but illustrating another alternative aspect for applying waist elastics.

Referring now to the drawings, a process for making garments to be worn about the lower torso is shown in its entirety at reference numeral 100 (FIGS. 1–3). The process 100 will be described in terms of making boxer shorts, or shorts, but it should be readily recognized that the process of the present invention may be equally applicable with pants, trunks, briefs, and other garments that may be worn about the lower torso and having a waist opening and a pair of hanging legs. It should be understood that the term "hanging legs" refers to the characteristic of the garment where the garment includes material that extends below the crotch of the garment and is intended to generally cover at least a portion of the leg of the wearer; the material may be loose fitting about the leg of the wearer or fit snugly about the leg of the wearer.

As representatively illustrated in FIGS. 1–3, The process 100 defines a machine direction indicated at the arrow marked 102, and a cross-machine direction indicated at the arrow marked 104 that is perpendicular to the machine direction 100. The process 100 also defines an orthogonal direction, indicated at the arrow marked 106 that is perpendicular to the plane created by the machine direction 102 and the cross machine direction 104. The process 100 is represented in the illustrated aspects with the orthogonal direction 106 being generally vertical. Nonetheless, as can be readily appreciated by those of skill in the art, the orthogonal direction 106 of the present invention may also be generally horizontal or otherwise oriented and still be within the scope of the present invention.

The process includes providing a first web 110 and a second web 120. The first web 110 and the second web 120 may be provided by separate webs, or may alternatively be provided by a single web that is folded in the machine direction 102 and then subsequently separated (not shown). The first web 110 defines a first web waist edge 112 and a first web leg edge 114 that is opposite the first web waist edge 112. The first web 110 also defines a first web interior surface 116, a first web exterior surface 118 that is opposite the first web interior surface 116, and a first leading chassis edge 160, particularly when the first web 110 is provided to the process 100.

The second web 120 defines a second web waist edge 122 and a second web leg edge 124 that is opposite the second web waist edge 122. The second web 120 also defines a second web interior surface 126, a second web exterior surface 128 that is opposite the second web interior surface 126, and a second leading chassis edge 162, particularly when the second web 120 is provided to the process 100. As representatively illustrated in FIGS. 1–3, the webs 110 and 120 may be provided in at least a partially facing relationship, and may be in a substantially completely facing relationship. For example, the second web interior surface 126 may be in at least a partially facing relationship with the first web interior surface 116. It should be noted that the first and second web interior and exterior surfaces 116, 118, 126, and 128 need not correspond to the inner and outer surfaces of the short when the short is produced.

The process 100 is illustrated in FIGS. 1–3 as being configured to have the webs 110 and 120 pass through the process 100 in a generally vertical orientation. Nonetheless, as can be readily appreciated by those of skill in the art, the process 100 may be configured to have the webs 110 and 120 pass through the process 100 in a generally horizontal orientation and still be within the scope of the present invention.

The webs 110 and 120 may be any suitable fabric to provide the shorts 10. In particular, the webs 110 and 120 may suitably be of materials which are comfortable against the skin and non-irritating. Since it is contemplated that the shorts 10 can be either disposable or durable, i.e., launderable, in the embodiments without an absorbent assembly, and disposable in the embodiments with an absorbent assembly, both nonwoven and woven materials are contemplated for the webs 110 and 120. For example, the webs can be selected from a wide variety of materials, including elastic, stretchable, or nonstretchable materials. Any other type of nonwoven laminate or woven or knitted fabric known to those skilled in the art can also be used. The webs 110 and 120 can be a single layer of material or a multi-layered laminate structure. Other suitable materials for the webs 110 and 120 include stretchable nonwovens, non-strechable nonwovens, and nonwoven laminates including spandex and/or stretchable film. Spandex is any of various elastic textile fibers made chiefly of polyurethane. LYCRA® is a brand of spandex commercially available from E.I. du Pont de Nemours and Company, Wilmington, Del., U.S.A. Alternatively, meltblown laminates are a suitable type of nonwoven laminate. It is desired that the webs 110 and 120 impart a relatively cloth-like texture to the shorts 10. The material for the webs 110 and 120 desirably, although not necessarily, has the ability to drape and conform to some extent to the body. In addition, the material can, but need not, be opaque. Finally, the material for the first web 110 may or may not be the same as the material in the second web 120.

The webs 110 and 120 may be provided by various methods as are known in the art. For example, the webs 110 and 120 may be unwound and drawn through the process 100 via driven rolls, belt conveyors, chain conveyors, and the like or combinations thereof (not shown).

As representatively illustrated in FIGS. 1–3, the webs 110 and 120 may be joined to one another with a bonding device 132 to provide a crotch seam 56. In particular aspects, spaced portions of the webs 110 and 120 may be joined to one another at selected locations to provide a plurality of crotch seams 56. The seams 56 may be substantially continuous, or may be provided by a series of intermittent bonds. The crotch seam 56 may be of various shapes to produce the desired result. For example, the crotch seam 56 may be generally rectilinear, or may be curvilinear, or generally "U" shaped as shown in the illustrated embodiments. In particular aspects, the crotch seam 56 may be curvilinear for improved fit and comfort.

In addition, as representatively illustrated in FIGS. 1–3, the crotch seam 56 may intersect the first and second web waist edges 112 and 122. Alternatively, the crotch seam 56 may begin and terminate completely within the surfaces 116, 118, 126 and 128 of the webs 110 and 120. In particular aspects, the crotch seam 56 may suitably intersect the first and second web waist edges 112 and 122 in two locations (FIGS. 1–3).

The first web 110 and the second web 120 may be joined by the bonding device 132 in various ways as are known in the art. For example, the crotch seam 56 may be formed by bonding the first and second webs 110 and 120 as they travel in the machine direction 102. This bonding can be accomplished by using ultrasonic or thermal bonding wheels rotating in a facing relationship on the exterior surfaces 118 and 128 of the webs 110 and 120 to form the crotch seam 56. For example, an anvil wheel and a horn wheel defining a nip can be used to form the crotch seam 56. Alternatively, any suitable bonding method known in the art can be used, such as adhesives, pressure bonding, sewing or the like.

The process 100 of the present invention may further include selectively removing portions of the webs 110 and 120. For instance, as representatively illustrated in FIGS. 1–3, the process 100 of the present invention may further include selectively removing a portion of the first web 110 at the first web waist edge 112. In addition, the process 100 of the present invention may include selectively removing a portion of the second web 120 at the second web waist edge 122. Further, as illustrated in FIGS. 1–3, the portions of the webs 110 and 120 that are removed are generally adjacent each other, and as such provide a crotch gap 54. Still further, the crotch seam 56 may suitably be located adjacent the crotch gap 54.

The removal of portions of the webs 110 and 120 can be accomplished by various methods as are known in the art. For example, the removal may be achieved by a cutting device 134 such as cutting rolls, a die cutting assembly, a water cutting device or an ultrasonic cutter, or combinations thereof. Alternatively, other suitable cutting methods known in the art can be used. The removal of portions of the webs 110 and 120 may happen to each web 110 or 120 individually or simultaneously. As representatively illustrated in FIGS. 1–3, the removal may suitably occur substantially simultaneously.

It should be noted that the joining of the webs 110 and 120 and the removal of portions of the webs 110 and 120 need not occur in a particular order, and moreover, need not happen sequentially. For example, the removal may occur prior to the joining of the webs 110 and 120 or alternatively, as representatively illustrated in FIGS. 1–3, the joining of the webs 110 and 120 may occur prior to the removal of portions of the webs 110 and 120. In yet another alternative, the joining of the webs 110 and 120 may occur at the same time as removal of portions of the web. This may be accomplished by utilizing an ultrasonic bonder that is also capable of cutting materials.

The process may further include the step of drawing the first web 110 from the second web 120 in the cross-machine direction 104. In particular, and as representatively illustrated in FIGS. 1–3, each of the webs 110 and 120 may be drawn away from the cross-directional centerline of the process 100. As used herein, the term "draw" or "drawing" refers to forcing an element in a particular direction, whether it be via a pulling force or a pushing force. The step of drawing the webs 110 and 120 away from each other defines a leading garment waist edge 152 and a trailing garment waist edge 154. Moreover, in aspects where the process 100 is being used to produce a series of shorts 10, the drawing of the webs 110 and 120 suitably occurs between a pair of adjacent crotch seams 56, and may place the ends of adjacent crotch seams 56 in nearly an abutting relationship. In a particular aspect, and as representatively illustrated in FIGS. 1–3, drawing the first web 110 from the second web 120 substantially bisects the distance between a pair of adjacent crotch seams 56.

It is contemplated that the drawing of the first web 110 from the second web 120 may be accomplished via the use of pins 130 that run on chains (not shown) underneath or above the webs 110 and 120. The pins 130 can be, for example, retractable pins described in U.S. Pat. Nos. 4,786,346 and 4,946,539, to Ales et al., both of which are herein incorporated by reference to the extent that they are consistent (i.e., not in conflict) herewith.

For example, a pair of corresponding pins 130 that diverge (i.e., that are attached to divergent drive chains)

could be used to separate the first and second webs 110 and 120 from one another. Corresponding pins 130 may advantageously travel for some distance at the same speed, to maintain the desired web separation as necessary through the process 100. Alternatively, the first and second webs 110 and 120 can be drawn away from each other by means other than pins, such as by vacuum, a combination of vacuum and pins, or other methods as are known in the art.

The process 100 can also include the step of slitting the webs 110 and 120. For example, at least a portion of the webs 110 and 120 may be slit generally in the orthogonal direction 106. The step of slitting the webs 110 and 120 may occur at a variety of points during the process; the webs 110 and 120 may be slit while the webs 110 and 120 are in the drawn condition or alternatively may be slit prior to the step of drawing the first web 110 from the second web 120. Thus, in one aspect, the webs 110 and 120 may be slit between successive crotch gaps 54 and/or successive crotch seams 56. In particular, the webs 110 and 120 may advantageously be slit proximate the location at which the webs 110 and 120 are being drawn in the cross-machine direction 104.

For example, as representatively illustrated in FIGS. 1–3, at least a portion of the first web 110 may be slit by a slitting device 136 between the first web leg edge 114 and the first web waist edge 112, and proximate where the webs 110 and 120 are being drawn in the cross-machine direction 104. In a particular aspect, the first web 110 may be slit in the orthogonal direction 106 from the first web leg edge 114 to proximate the first web waist edge 112, without severing the first web waist edge 112 (FIGS. 1 and 2). Alternatively, and as will be discussed in greater detail below, first web 110 may be entirely slit from the first web leg edge 114 to the first web waist edge 112 (FIG. 3). Similarly, the second web 120 may be slit in the orthogonal direction 106 from the second web leg edge 124 to proximate the second web waist edge 122, without severing the second web waist edge 122 (FIGS. 1 and 2). Alternatively, and as will be discussed in greater detail below, second web 120 may be entirely slit from the second web leg edge 124 to the second web waist edge 122 (FIG. 3).

As representatively illustrated in FIGS. 1–3, the step of slitting the first web 110 and the second web 120 may further provide a first trailing chassis edge 156 and a second trailing chassis edge 158. Slitting the first web 110 and the second web 120 can also define a garment chassis 150 including a portion of the first web 110 and a portion of the second web 120 between the first and second leading chassis edges 160 and 162 and the first and second trailing chassis edges 156 and 158 and joined at the crotch seam 56. Further, the garment chassis may also be between the leading garment waist edge 152 and the trailing garment waist edge 154.

In addition, in aspects where the process 100 is configured to make a series of shorts 10, the step of slitting the first web 110 and the second web 120 may provide the first leading chassis edge 160 and the second leading chassis edge 162 for next or subsequent garment chassis 150 to be produced by the process 100. The slitting of the first and second webs 110 and 120 can be achieved by various methods. For example, the webs may be slit using a die cutter, a rotary slitter, a water cutter, an ultrasonic cutting device, a device for tearing the webs, and the like or combinations thereof.

The process 100 of the present invention may also include extending the garment chassis 150 in the machine direction 102 to elongate the garment chassis 150 prior to attaching an absorbent assembly 60. As will be discussed in greater detail below, elongating the garment chassis 150, and thus extending the crotch seam 56, advantageously presents a relatively flat surface upon which an absorbent assembly 60 may be more readily and reliably attached.

As may be readily appreciated, the step of drawing the first and second webs 110 and 120 away from each other can provide a complementary action to extending the garment chassis 150. That is, the action of drawing the webs 110 and 120 in a cross machine direction 104 can serve to also elongate the garment chassis 150 in the machine direction 102. Alternatively, the garment chassis 150 may be extended by accelerating the pins 130 as necessary during the process 100 downstream in the machine direction 102. In still yet another alternative, elongating the garment chassis 150 may be accomplished by accelerating the garment chassis downstream in the machine direction 102, such as by a vacuum conveyor or a pair of nip rolls (not shown).

In particular aspects of the present invention, the process 100 may include attaching an absorbent assembly 60 to the garment chassis. For example, as representatively illustrated in FIGS. 1–3 and as mentioned above, the absorbent assembly 60 may suitably be attached to the garment chassis 150 while it is in an elongated condition. The absorbent assembly 60 may be attached to the garment chassis 150 by a variety of methods as are known in the art. For example, the absorbent assembly 60 may be attached to the garment chassis 150 by adhesives, ultrasonic bonding, pressure bonding, sewing, and the like or combinations thereof.

Moreover, the absorbent assembly 60 may be releasably attached to the garment chassis 150. Such a configuration may be advantageous where the short 10 is arranged to be durable or semi-durable, but yet still include an absorbent assembly 60. For example, the absorbent assembly 60 may be releasably attached to the garment chassis using hook and loop fasteners or a cohesive material.

The absorbent assembly 60 may be arranged with the garment chassis 150 in a variety of ways. For example, the absorbent assembly 60 may be disposed along the crotch seam 56 in the garment chassis 150. As used herein, the term "disposed on" or "disposed along" and variations thereof are intended to mean that one element can be integral with another element, or that one element can be a separate structure bonded to or placed with or placed near another element. In addition, the absorbent assembly 60 may be attached to the garment chassis at the garment waist edges 152 and 154.

The process 100 may further include the step of separating the garment chassis 150 from the first web 110 and the second web 120. In configurations where the webs 110 and 120 are not completely slit from the web leg edges 114 and 124 to the web waist edges 112 and 122 (FIGS. 1 and 2), the garment chassis 150 may be separated from the webs 110 and 120 by a separation device 138 that cuts the remaining portions of the webs 110 and 120, such as by a die cutter, a water cutter, a rotary cutter, ultrasonic cutting, and the like. Alternatively, the step of slitting the webs 110 and 120 may be configured to place a line of weakness (not shown), such as perforations, in the portions of the webs 110 and 120 that connect the garment chassis 150 with the webs 110 and 120. As such, the lines of weakness may be broken by an application of force drawing the garment chassis in the machine direction 102 downstream in the process 100. Such a force may be applied by drawing the garment chassis 150 through a nip that accelerates the garment chassis in the machine direction 102, or by further diverging a pair of corresponding pins 130 in the cross machine direction 104.

Alternatively, the webs 110 and 120 may be completely slit from the web leg edges 114 and 124 to the web waist edges 112 and 122 (FIG. 3). In such a configuration, the garment chassis 150 may remain connected to the webs 110 and 120 in a variety of ways. For example, the garment chassis 150 may remain connected to the webs 110 and 120 via a waist elastic 58. As will be described in greater detail below, a waist elastic 58 may be applied to the first web waist edge 112 and the second web waist edge 122. As representatively illustrated in FIG. 3, the waist elastic 58 may overlap the leading garment waist edge 152 and the trailing garment waist edge 154 in an adjacently located configuration. That is, in arrangements where the process 100 is intended to continuously produce a series of shorts 10, the waist elastic 58 overlaps and connects the trailing garment waist edge 154 of one garment chassis 150 to the leading garment waist edge 152 of the subsequent garment chassis 150 in the process 100. Thus, the garment chassis 150 may be separated from the webs 110 and 120 by cutting the waist elastic 58 in the cross-machine direction 104, suitably between adjacent garment waist edges 152 and 154. Moreover, separating the absorbent chassis from the webs 110 and 120 in such a manner may be utilized to cut an absorbent assembly 60 that is provided as a continuous web and has been attached to the garment chassis 150. In an aspect as described above, the separating may be accomplished by passing the garment chassis 150 in a relatively flat condition through separation device 138 that is a registered knife and anvil roll. Alternatively, the waist elastic 58 may be cut via a water cutter, an ultrasonic cutter, or another cutting device previously described herein, or combinations thereof.

Figure 4:
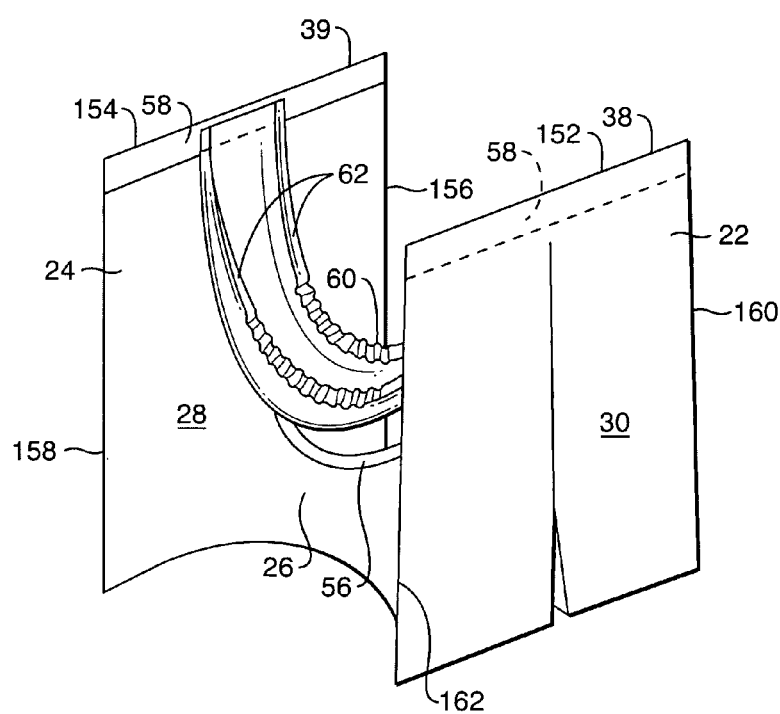
FIG. 4 representatively illustrates a perspective view of a partially completed garment made by one aspect of the process of the present invention.
Figure 5:
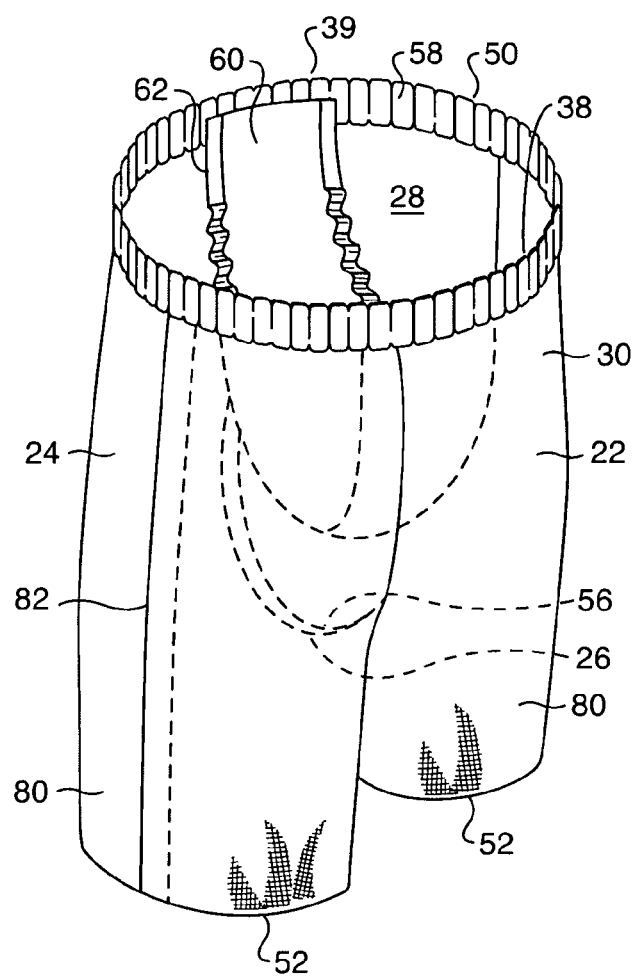
FIG. 5 representatively illustrates a perspective view of a completed garment made by one aspect of the process of the present invention.

Upon separation of the garment chassis 150 from the webs 110 and 120, the garment chassis may be fastened together to provide the garment 10. For instance, as representatively illustrated in FIG. 4, the short 10 may be provided by fastening the first leading chassis edge 160 to the first trailing chassis edge 156. Likewise, the second leading chassis edge 162 may be fastened to the second trailing chassis edge 158. Accordingly a short 10 with a waist opening 50 and a pair of hanging legs 80 is provided (FIG. 5).

In a particular aspect, the fastening of the first leading chassis edge 160 to the first trailing chassis edge 156 and the second leading chassis edge 162 to the second trailing chassis edge 158 form a pair of side seams 82. The side seams 82 can take any number of forms, including both refastenable and non-refastenable seams as is known in the art. The provision of the side seams 82 can be accomplished in the manner described in U.S. Pat. No. 5,046,272, issued Sep. 10, 1991 to Vogt et al., or in the manner described in PCT Publications WO 01/87562 by Tomsovic, et al., WO 01/87217 by Durrance, et al., WO 01/87753 by Csida et al., and/or WO 01/87218 by Vogt, et al., all of which are incorporated herein by reference to the extent they are consistent (i.e., not in conflict) herewith. In particular and as representatively illustrated in FIGS. 1–3, the chassis edges 156, 158, 160 and 162 may be brought together to form side seams 82 by a folding device 140 that folds the garment chassis 150 upon itself generally at its machine direction center line, thereby bringing the garment waist edges 152 and 154 of the garment chassis 150 together. The folding of the garment chassis 150 may be accomplished by folding devices known in the art, such as a blade folder.

As is known in the art, the side seams 82 can be inward or outward butt seams (not shown) or lap seams (FIGS. 1–3 and 5). It is contemplated that the side seams 82 may be fastened only along a portion of the distance between the waist opening 50 and the leg openings 52. For instance, the seams 82 may be fastened at the waist opening 50, leaving a slit open above the leg openings 52, such as in the style of some running or athletic garments. Alternatively, the side seams 82 may be fastened from the garment waist edges 152, 154 (and thus the waist opening 50) to the web leg edges 114 and 124 (and thus to the respective leg openings 52).

As mentioned above, the process 100 may also include applying a waist elastic 58. The waist elastic may be applied to the webs 110 and 120 in a variety of locations. In a particular aspect and as representatively illustrated in FIG. 2, the waist elastic 58 may be applied proximate the first web waist edge 112 and the second web waist edge 122. Moreover, the waist elastic 58 may be applied to the first web interior surface 116 and the second web interior surface 126. Alternatively, the waist elastic 58 may be applied to the first web exterior surface 118 and the second web exterior surface 128. In yet another alternative, the waist elastic 58 may be applied to the first web exterior and interior surfaces 116 and 118 and the second web interior and exterior surfaces 126 and 128. In a particular aspect (FIG. 2), the waist elastic 58 can be applied proximate the first web waist edge 112 on the first web exterior surface 118 and proximate the second web waist edge 122 on the second web exterior surface 128.

In the aspect described above, the waist elastic 58 may be introduced into the process in a number of locations. For example, as representatively illustrated in FIG. 2, the waist elastic 58 may be continuously provided into the process prior to removing the portions of the webs 110 and 120 in order to form the crotch gap 54. As such, a corresponding portion of the waist elastic 58 may also be removed, as representatively illustrated in FIG. 2.

Alternatively, in another aspect, the waist elastic may be introduced into the process in an intermittent fashion. For instance, as representatively illustrated in FIG. 3, discrete portions of waist elastic 58 may be applied to the webs 110 and 120 in selected areas. In particular and as described above, a portion of waist elastic may be cut and placed in the process 100 to overlap and connect adjacent leading garment waist edges 152 and trailing garment waist edges 154 of adjacent garment chassis 150 where the process 100 is arranged to continuously make shorts 10.

The waist elastic 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic 58 includes a plurality of dry-spun coalesced multifilament spandex elastomeric threads sold under the trade name LYCRA® and available from E.I. du Pont de Nemours and Company, Wilmington, Del., U.S.A. In particular embodiments, the elastic material includes a stretch-thermal laminate (STL), a neck-bonded laminated (NBL), a reversibly necked laminate, or a stretch-bonded laminate (SBL) material. Methods of making such STL, NBL and SBL materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the names of Taylor et al.; PCT Publication WO 01/88245 published on Nov. 22, 2001 in the names of Welch, et al.; all of which are incorporated herein by reference to the extent that they are consistent (i.e., not in conflict) herewith. Alternatively, the waist elastic 58 can include other woven or nonwoven materials, such as stretchable but inelastic materials.

As another alternative, the waist elastic 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158, issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference to the extent they are consistent (i.e., not in conflict) herewith. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material can comprise elastomeric or nonelastomeric materials. Suitable nonelastomeric retractive materials can comprise without limitation polyether block amides (PEBAX®) or the like, and laminates thereof. Suitable elastomeric retractive materials can comprise without limitation LYCRA® materials, elastomeric materials including latex or rubber or synthetic urethanes, or the like, and laminates thereof. In particular embodiments, the retractive material can comprise an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference to the extent they are consistent (i.e., not in conflict) herewith.

As mentioned above, the process 100 may include attaching an absorbent assembly 60 to the garment chassis 150. Any suitable absorbent assembly can be used for the absorbent assembly 60. The absorbent assembly 60 can be any structure which is generally compressible, conformable, non-irritating to the skin, and capable of absorbing and retaining liquids and certain body wastes. The absorbent assembly 60 can be manufactured in a wide variety of sizes and shapes, from a wide variety of liquid absorbent materials commonly used in the art, and may be stretchable, non-stretchable, or elastic. For example, the absorbent assembly 60 can suitably include a matrix of hydrophilic fibers, such as a web of cellulosic fluff, mixed with particles of a high-absorbency material commonly known as superabsorbent material. In a particular embodiment, the absorbent assembly 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 60 to better contain and absorb body exudates. The concentration of the superabsorbent particles can also vary through the thickness of the absorbent assembly 60. Alternatively, the absorbent assembly 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 60 includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 60 in an amount of from 0 to about 90 weight percent based on total weight of the absorbent assembly. The absorbent assembly 60 suitably has a density within the range of about 0.10 to about 0.35 grams per cubic centimeter. The absorbent assembly 60 may or may not be wrapped or encompassed by a suitable wrap that may help maintain the integrity and/or shape of the absorbent assembly.

The absorbent assembly 60 can also incorporate other materials that are designed primarily to receive, temporarily store, and/or transport liquid along the mutually facing surface with absorbent assembly 60, thereby maximizing the absorbent capacity of the absorbent assembly. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

The absorbent assembly may also include a liner material that is intended to face the wearer in use. The liner can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the liner. For example, the liner can be composed of a meltblown or spunbonded web of polyolefin fibers. The liner can also be a bonded-carded web composed of natural and/or synthetic fibers. The liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. The surfactant can be applied by any conventional means, such as spraying, printing, brush coating or the like. The surfactant can be applied to the entire liner or can be selectively applied to particular sections of the liner, such as the medial section along the longitudinal center line.

A suitable liquid permeable liner is a nonwoven bicomponent web having a basis weight of about 27 gsm. The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan.

The absorbent assembly 60 may also include a suitable outercover intended to face away from the body of the wearer in use. The outercover desirably comprises a material that is substantially liquid impermeable. The outercover can be a single layer of liquid impermeable material, or may be a multi-layered laminate structure in which at least one of the layers is liquid impermeable. For instance, the outercover can include a liquid permeable outer layer and a liquid impermeable inner layer that are suitably joined together by a laminate adhesive. The liquid permeable outer layer can be any suitable material and desirably one that provides a generally cloth-like texture. One example of such a material is a 20 gsm spunbond polypropylene nonwoven web. The outer layer can also be made of those materials of which liquid permeable liner is made. While it is not a necessity for outer layer to be liquid permeable, it is desired that it provides a relatively cloth-like texture to the wearer.

The inner layer of the outercover can be both liquid and vapor impermeable, or can be liquid impermeable and vapor permeable. The inner layer is desirably manufactured from a thin plastic film, although other flexible liquid impermeable materials can also be used. The inner layer, or the liquid impermeable outercover when a single layer, prevents waste material from wetting articles, such as bedsheets and clothing, as well as the wearer and caregiver. A suitable liquid impermeable film for use as liquid impermeable inner layer, or a single layer liquid impermeable outercover, is a 0.025 millimeter (1.0 mil) polyethylene film commercially available from Edison Plastics Company of South Plainfield, N.J. The liquid impermeable material can also be configured to permit vapors to escape from the interior of the absorbent body, while still preventing liquids from passing through the outercover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

In particular embodiments, the absorbent assembly 60 is thin to provide a slim, comfortable, non-bulky short 10. Any suitable thin absorbent assembly may be used, such as for example, the thin absorbent described in WO 02/49565, published Jun. 27, 2002, by Sawyer et al., which is incorporated herein by reference to the extent it is consistent (i.e., not in conflict) herewith.

The absorbent assembly 60, desirably although not necessarily, includes a pair of containment flaps 62 (FIGS. 4 and 5) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration in at least the crotch region 26 of the short 10 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference to the extent that it is consistent (i.e. not in conflict) herewith.

In the alternative, a pant-like garment insert could be used for the absorbent assembly 60. For example, the pant-like garment insert suitably includes a body side liner, an outer cover, an absorbent assembly between the body side liner and the outer cover, and side panels. Example of suitable inserts include a training pant, such as HUGGIES® PULL-UPS® Disposable Training Pants, and disposable underpants, such as GOODNIGHTS® Disposable Underpants, both manufactured by Kimberly-Clark Corporation, Neenah, Wis., U.S.A.

As another alternative, a pad-type absorbent could be used for the absorbent assembly. The pad-type absorbent can be attached in the crotch-region 26 of the short 10. An example of a suitable pad-type absorbent is a feminine care pad such as KOTEX® Feminine Napkins, KOTEX® LIGHTDAYS® Pantiliners, or an incontinence absorbent pad such as POISE® Feminine Guards and Pads or DEPEND® Guards for Men, all manufactured by Kimberly-Clark Corporation, Neenah, Wis., U.S.A.

As representatively illustrated in FIG. 5, an embodiment of a short 10 produced by the process 100 of the present invention can include a front region 22, a back region 24, a crotch region 26, an inner surface 28 which is configured to contact the wearer, and an outer surface 30 opposite the inner surface 28 which is configured to face away from the surface of the wearer's body. The short 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the short 10 which, when worn, is positioned on the front of the wearer while the back region 24 includes the portion of the short 10 which, when worn, is positioned on the back of the wearer. The crotch region 26 of the short 10 includes the portion of the short which, when worn, is positioned between the legs of the wearer and covers the lower torso of the wearer.

As illustrated in FIG. 5, the front and back regions 22 and 24 are joined together at side seams 82 and the left and right sides of the short 10 are joined together at the crotch seam 56 to define a three-dimensional short configuration having a waist opening 50 and a pair of hanging legs 80 with leg openings 52. In particular aspects, the crotch seam 56 may follow a path which begins substantially at the front waist edge 38, extends through the crotch region 26, and terminates substantially at the back waist edge 39. In alterative embodiments, the crotch seam 56 can follow a path which begins below the front waist edge 38 on the front region 22 and terminates below the back waist edge 39 on the back region 24. As is known in the art, the crotch seam 56 can be an inward butt seam or a lap seam (not shown). In the alternative, the crotch seam 56 can be an outward butt seam.

In particular embodiments and as mentioned above, the short 10 can include an absorbent assembly 60. The absorbent assembly 60 can be attached to the short 10 at the front waist edge 38 and back waist edge 39, or at some point below the front waist edge 38 and back waist edge 39 on the front region 22 and back region 24. Alternatively or additionally, the absorbent assembly 60 can be attached to the pant 10 in the crotch region 26.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A process for making a garment having a waist opening and a pair of hanging legs, said process defining a machine direction, a cross-machine direction and an orthogonal direction that is perpendicular to a plane created by said machine direction and said cross-machine direction, said process comprising:
   providing a first web defining a first web waist edge, a first web leg edge, a first leading chassis edge, a first web interior surface and a first web exterior surface;
   providing a second web defining a second web waist edge, a second web leg edge, a second leading chassis edge, a second web interior surface and a second web exterior surface, said second web interior surface being disposed in a facing relationship with said first web interior surface;
   joining said first web to said second web to provide a crotch seam;
   selectively removing a portion of said first web at said first web waist edge and a portion of said second web at said second web waist edge to form a crotch gap;
   drawing said first web from said second web in said cross-machine direction;
   slitting at least a portion of said first web between said first web leg edge and said first web waist edge;
   slitting at least a portion of said second web between said second web leg edge and said second web waist edge, wherein said slitting of said first web and said second web provides a first trailing chassis edge, a second trailing chassis edge and defines a garment chassis comprising said first web and said second web between said first and said second leading and trailing chassis edges and joined at said crotch seam; and
   fastening said first leading chassis edge to said first trailing chassis edge and said second leading chassis edge to said second trailing chassis edge to provide said garment having said waist opening and said pair of hanging legs.

2. The process of claim 1 wherein fastening said leading chassis edges to said trailing chassis edges forms a pair of side seams and wherein said side seams are lap seams.

3. The process of claim 1 wherein fastening said leading chassis edges to said trailing chassis edges forms a pair of side seams and wherein said side seams are refastenable.

4. The process of claim 1 wherein fastening said leading chassis edges to said trailing chassis edges forms a pair of side seams and wherein said side seams are fastened from said waist edges to said leg edges.

5. The process of claim 1 wherein said crotch seam intersects said first web waist edge and said second web waist edge at two locations.

6. The process of claim 1 comprising attaching an absorbent assembly to said garment chassis.

7. The process of claim 6 wherein said absorbent assembly is releasably attached to said garment chassis.

8. The process of claim 6 wherein said absorbent assembly is disposed along said crotch seam.

9. The process of claim 6 wherein said absorbent assembly is attached to said garment waist edges.

10. The process of claim 1 wherein said crotch seam is adjacent said crotch gap.

11. The process of claim 1 comprising applying a waist elastic proximate said first web waist edge and said second web waist edge.

12. The process of claim 11 wherein said waist elastic is applied proximate said first web waist edge on said first web exterior surface and proximate said second web waist edge on said second web exterior surface.

13. The process of claim 1 wherein said process is configured to make a series of said garments and wherein slitting said first web and said second web provides said first leading chassis edge and said second leading chassis edge for a subsequent garment chassis.

14. A continuous process for making garments having a waist opening and a pair of hanging legs, said process defining a machine direction, a cross-machine direction and an orthogonal direction that is perpendicular to a plane created by said machine direction and said cross-machine direction, said process comprising:
   providing a first web traveling in a machine direction and defining a first web waist edge, a first web leg edge, a first leading chassis edge, a first web interior surface and a first web exterior surface;
   providing a second web traveling in a machine direction and defining a second web waist edge, a second web leg edge, a second leading chassis edge, a second web interior surface and a second web exterior surface, said second web interior surface being disposed in a facing relationship with said first web interior surface;
   joining said first web to said second web at a crotch seam;
   selectively removing a portion of said first web at said first web waist edge and a portion of said second web at said second web waist edge to provide a crotch gap;
   drawing said first web from said second web in said cross-machine direction to define a leading garment waist edge and a trailing garment waist edge;
   slitting at least a portion of said first web between said first web leg edge and said first web waist edge, and a portion of said second web between said second web leg edge and said second web waist edge, wherein said slitting of said first web and said second web provides a first trailing chassis edge, a second trailing chassis edge and defines a garment chassis comprising said first web and said second web between said first and said second leading and trailing chassis edges and joined at said crotch seam; and
   fastening said first leading chassis edge to said first trailing chassis edge and said second leading chassis edge to said second trailing chassis edge to provide said garment having said waist opening and said pair of hanging legs.

15. The process of claim 14 wherein fastening said leading chassis edges to said trailing chassis edges forms a pair of side seams and wherein said side seams are refastenable.

16. The process of claim 14 wherein fastening said leading chassis edges to said trailing chassis edges forms a pair of side seams and wherein said side seams are fastened from said waist edges to said leg edges.

17. The process of claim 14 comprising attaching an absorbent assembly to said garment chassis.

18. The process of claim 17 wherein said absorbent assembly is releasably attached to said garment chassis.

19. The process of claim 17 wherein said absorbent assembly is disposed along said crotch seam.

20. The process of claim 17 wherein said absorbent assembly is attached to said garment waist edges.

21. The process of claim 14 comprising extending said garment chassis in said machine direction to elongate said garment chassis prior to attaching said absorbent assembly.

22. The process of claim 14 wherein said crotch seam is adjacent said crotch gap.

23. The process of claim 14 wherein drawing said first web from said second web substantially bisects the distance between a pair of adjacent crotch seams.

24. The process of claim 14 comprising applying a waist elastic proximate said first web waist edge and said second web waist edge.

25. The process of claim 14 wherein said waist elastic is applied proximate said first web waist edge on said first web exterior surface and proximate said second web waist edge on said second web exterior surface.

26. The process of claim 25 wherein said waist elastic overlaps said leading garment waist edge and said trailing garment waist edge in an adjacently located configuration.

27. The process of claim 14 wherein said process is configured to make a series of said garments and wherein slitting said first web and said second web provides said first leading chassis edge and said second leading chassis edge for a subsequent garment chassis.

28. A continuous process for making garments having a waist opening and a pair of hanging legs, said process defining a machine direction, a cross-machine direction and an orthogonal direction that is perpendicular to a plane created by said machine direction and said cross-machine direction, said process comprising:
provproviding a first web traveling in a machine direction and defining a first web waist edge, a first web leg edge, a first leading chassis edge, a first web interior surface and a first web exterior surface;
providing a second web traveling in a machine direction and defining a second web waist edge, a second web leg edge, a second leading chassis edge, a second web interior surface and a second web exterior surface, said second web interior surface being disposed in a facing relationship with said first web interior surface;
joining said first web to said second web at selected locations to provide a plurality of spaced crotch seams;
removing portions of said first web at said first web waist edge and corresponding portions of said second web at said second web waist edge to provide a plurality of crotch gaps;
drawing said first web from said second web in said cross-machine direction to define a leading garment waist edge and a trailing garment waist edge;
slitting at least a portion of said first web between said first web leg edge and said first web waist edge, and a portion of said second web between said second web leg edge and said second web waist edge, wherein said slitting of said first web and said second web provides a first trailing chassis edge, a second trailing chassis edge and defines a garment chassis comprising said first web and said second web between said first and said second leading and trailing chassis edges and joined at a crotch seam;
extending said garment chassis in said machine direction to elongate said garment chassis;
attaching an absorbent assembly to said garment chassis, wherein said absorbent assembly is disposed along said crotch seam;
separating said garment chassis from said first web and said second web; and
fastening said first leading chassis edge to said first trailing chassis edge and said second leading chassis edge to said second trailing chassis edge to provide said garment having said waist opening and said pair of hanging legs.

29. The process of claim 28 wherein fastening said leading chassis edges to said trailing chassis edges forms a pair of side seams and wherein said side seams are refastenable.

30. The process of claim 28 comprising applying a waist elastic proximate said first web waist edge and said second web waist edge.

31. The process of claim 30 wherein said waist elastic is applied proximate said first web waist edge on said first web exterior surface and proximate said second web waist edge on said second web exterior surface.

32. The process of claim 30 wherein said waist elastic overlaps said leading garment waist edge and said trailing garment waist edge in an adjacently located configuration.

33. A process for making garments, said process defining a machine direction, a cross-machine direction and an orthogonal direction that is perpendicular to a plane created by said machine direction and said cross-machine direction, said process comprising:
providing a first web defining a first web waist edge, a first web leg edge, a first leading chassis edge, a first web interior surface and a first web exterior surface;
providing a second web defining a second web waist edge, a second web leg edge, a second leading chassis edge, a second web interior surface and a second web exterior surface, said second web interior surface being disposed in a facing relationship with said first web interior surface;
joining said first web to said second web to provide a crotch seam;
selectively removing a portion of said first web at said first web waist edge and a portion of said second web at said second web waist edge to form a crotch gap;
drawing said first web from said second web in said cross-machine direction;
slitting at least a portion of said first web between said first web leg edge and said first web waist edge;
slitting at least a portion of said second web between said second web leg edge and said second web waist edge, wherein said slitting of said first web and said second web provides a first trailing chassis edge, a second trailing chassis edge and defines a garment chassis comprising said first web and said second web between said first and said second leading and trailing chassis edges and joined at said crotch seam.

34. A process for making garments having a waist opening and a pair of hanging legs, said process comprising:
providing a first web traveling in a machine direction;
providing a second web traveling in a machine direction;
joining spaced portions of said first and second webs to define a plurality of crotch seams;
selectively removing portions of said first and second webs to provide a plurality of crotch gaps;
drawing said first web from said second web in a cross-machine direction at locations disposed between successive crotch gaps;
slitting said first web and said second web between successive crotch gaps to form a plurality of garment chasses, each garment chassis comprising a first web portion and a second web portion joined at a crotch seam; and
fastening said first web portion to itself and said second web portion to itself to form a garment having a waist opening and a pair of hanging legs.

* * * * *